United States Patent
Soon-Shiong et al.

(10) Patent No.: US 12,274,748 B2
(45) Date of Patent: Apr. 15, 2025

(54) ADENOVIRAL VECTOR TRANSDUCED APHERESIS PRODUCT

(71) Applicant: ImmunityBio, Inc., Culver City, CA (US)

(72) Inventors: Patrick Soon-Shiong, Culver City, CA (US); Elizabeth Gabitzsch, Culver City, CA (US); Philip T. Liu, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 0 days.

(21) Appl. No.: 18/649,790

(22) Filed: Apr. 29, 2024

(65) Prior Publication Data

US 2024/0366764 A1  Nov. 7, 2024

Related U.S. Application Data

(60) Provisional application No. 63/500,235, filed on May 4, 2023.

(51) Int. Cl.

| | | |
|---|---|---|
| *A61K 40/15* | (2025.01) | |
| *A61K 40/24* | (2025.01) | |
| *A61K 40/42* | (2025.01) | |
| *C07K 14/47* | (2006.01) | |
| *C12N 5/0783* | (2010.01) | |
| *C12N 15/86* | (2006.01) | |

(52) U.S. Cl.
CPC .......... *A61K 40/4201* (2025.01); *A61K 40/15* (2025.01); *A61K 40/24* (2025.01); *C07K 14/4748* (2013.01); *C12N 5/0646* (2013.01); *C12N 15/86* (2013.01); *C12N 2501/22* (2013.01); *C12N 2501/2315* (2013.01); *C12N 2501/26* (2013.01); *C12N 2710/10343* (2013.01); *C12N 2710/10362* (2013.01)

(58) Field of Classification Search
None
See application file for complete search history.

(56) References Cited

U.S. PATENT DOCUMENTS

| | | | |
|---|---|---|---|
| 10,695,417 B2 * | 6/2020 | Jones | A61K 38/19 |
| 2004/0033605 A1 * | 2/2004 | Havenga | C12N 15/86 |
| | | | 435/456 |
| 2017/0165341 A1 | 6/2017 | Jones et al. | |
| 2017/0368161 A1 | 12/2017 | Jones et al. | |
| 2019/0022209 A1 | 1/2019 | Jones et al. | |
| 2019/0388536 A1 * | 12/2019 | Chen | A61K 39/42 |
| 2021/0260175 A1 | 8/2021 | Jones et al. | |
| 2021/0361711 A1 * | 11/2021 | Duggal | C07K 14/54 |
| 2024/0226266 A1 * | 7/2024 | Balint | A61P 35/00 |

FOREIGN PATENT DOCUMENTS

| | | | |
|---|---|---|---|
| WO | WO2016172249 | * | 4/2016 |
| WO | 2017205810 A1 | | 11/2017 |
| WO | WO2023094993 | * | 11/2022 |

OTHER PUBLICATIONS

International Search report and Written Opinion received for PCT/US24/26806 dated Aug. 16, 2024, 12 pages.
Nair et al., "Isolation and Generation of Human Dendritic Cells", Curr Protoc Immunol., Nov. 2012, Chapter 7, 31 pages.
Palucka and Banchereau, "Cancer Immunotherapy via Dendritic Cells", Nat Rev Cancer. Mar. 22, 2012; 12(4), 265-77, 30 pages.
Pham et al., "Enhancement of antitumor effect using dendritic cells activated with natural killer cells in the presence of Toll-like receptor agonist", Exp Mol Med 42, 407-419 (2010), 13 pages.
Reid et al., "Intravascular adenoviral agents in cancer patients: lessons from clinical trials", Cancer Gene Ther. Dec. 2002; 9(12): 979-86, p. 08.

* cited by examiner

*Primary Examiner* — Michail A Belyavskyi
(74) *Attorney, Agent, or Firm* — Martin Fessenmaier; Umberg Zipser LLP

(57) ABSTRACT

An immunotherapeutic composition is contemplated that comprises subject-derived peripheral blood mononuclear cells (PBMC) and at least one recombinant adenovirus subtype 5 (Ad5) comprising a deletion in an E1 gene region, a deletion in an E2b gene region, and a nucleic acid sequence encoding a peptide antigen, wherein the PBMC are exposed ex-vivo to the at least one Ad5 vector. Advantageously, the same PBMC composition may also be used to prepare modified NK cells, and especially modified NK include CIML NK cells, CENK cells and mCENK cells.

6 Claims, 5 Drawing Sheets

ADENOVIRAL VECTOR TRANSDUCED APHERESIS PRODUCT

This application claims priority to our U.S. Provisional application with the Ser. No. 63/500,235, which was filed May 4, 2023, and which is incorporated by reference herein.

FIELD OF THE INVENTION

The field of the invention is compositions and method for cancer treatment, especially as it relates to treatment of a subject using ex vivo modified apheresis product in which cells are transfected with a recombinant therapeutic virus, and optionally in which cells are differentiated or transfected to express a chimeric antigen receptor.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer vaccines, and particularly viral cancer vaccines, have shown much promise in recent years but are often limited due to various factors, including immunogenicity of the viral vehicle and/or poor presentation of the recombinant (neo)antigen. In an effort to improve therapeutic effect of cancer vaccines, selected neoepitopes can be subjected to an ex vivo test protocol in which an immune response of a patient's immune cells is determined before administration of a vaccine that contains the selected neoepitopes as is described in WO 2018/106699. While conceptually attractive, the selected neoepitopes are typically encoded in a recombinant viral nucleic acid, and the so produced viral vaccine is then administered to a patient. Unfortunately, due to the typically systemic delivery of viral vehicles, pervasive training of the various components in the immune system (e.g., dendritic cells, CD8+ T-cells, CD4+ helper T-cells, B-cells) is often not or only poorly achieved. Moreover, even where antigen presentation is achieved to at least some degree, a therapeutically effective immune response may not be generated, for example, due to relatively low quantities of the viral vehicle. These difficulties are often further exacerbated by significant hepatotoxicity and often rapid attachment of the recombinant viral particles to the host cells, leading to various side effects and even death (see e.g., *Cancer Gene Therapy* (2002) 9, 979-986).

To overcome some of the difficulties that are associated with the systemic delivery of tumor antigens, various efforts have been undertaken to trigger in vitro stimulation of certain cells of the immune system. For example, in one approach, dendritic cells were incubated with NK cells to generate mature dendritic cells in the presence of TLR agonists (see e.g., *Experimental & Molecular Medicine* (2010), 42(6), p 407-419). In another approach, antigen presenting cells were stimulated with chimeric proteins comprising cancer specific antigens (see e.g., *Nat Rev Cancer;* 12(4): 265-277). Here, antigens were directly delivered to dendritic cells (DC) in vivo using chimeric proteins comprising an antibody that was specific for a DC receptor fused to a selected antigen. Such specific targeting of antigens to DCs in vivo elicited potent antigen-specific CD4+ and CD8+ T cell-mediated immunity. However, the induction of immunity also required the provision of DC maturation signals. Otherwise, such approach induced antigen-specific tolerance, which is opposite of the desired outcome. Moreover, currently known in vitro DC targeting using DC receptors requires the generation of bespoke molecular entities, which is both time and resource intensive. In addition, such approach also needed specific maturation signal which further complicates a vaccination strategy.

In still further options to reduce systemic exposure, therapeutic viruses can be administered via subcutaneous route. While such route of administration will significantly reduce the risk of serious adverse events, additional problems arise. Most significantly, subcutaneous administration will substantially limit exposure of the virus to antigen presenting cells, and particularly dendritic cells. As such, the expected therapeutic effect is much less than with systemic administration.

Thus, even though various compositions and methods for cancer vaccines are known in the art, all or almost all of them suffer from several drawbacks, particularly where the cancer vaccine uses recombinant viral vehicles to generate neoantigens in infected cells. Therefore, there remains a need for improved viral vaccine compositions.

SUMMARY OF THE INVENTION

The inventive subject matter is directed to various compositions and methods of viral vaccine compositions in which donor cells, including peripheral blood mononuclear cells (PBMC) of a subject are ex vivo infected with a recombinant viral vaccine to a degree sufficient to reduce or even entirely deplete the composition of free extracellular viral particles, thereby avoiding adverse effects otherwise likely to occur. In further contemplated compositions and methods, at least some of the donor cells, and especially the lymphocytes, are further genetically modified, for example to express a CAR, and/or are treated to differentiate to more mature immune cells. Most preferably, the ex vivo infection of the PBMC is preferential or even selective with regard to dendritic cells and is further preferably performed in the presence of other immune cells such as macrophages, monocytes, T cells, B cells, etc.

In one aspect of the inventive subject matter, the inventors contemplate an immunotherapeutic composition that includes subject-derived peripheral blood mononuclear cells (PBMC) and at least one recombinant adenovirus subtype 5 (Ad5) vector having a deletion in an E1 gene region, a deletion in an E2b gene region, and a nucleic acid sequence encoding a peptide antigen, wherein the PBMC are exposed ex-vivo to the Ad5 vector. Most typically, the Ad5 vector comprises a nucleic acid for expression of at least one of a tumor associated antigen, a neoantigen, a cytokine, a gene therapy, and an immune modulating protein.

As will be readily appreciated, contemplated immunotherapeutic compositions may further include IL15 or an interleukin 15:interleukin 15 receptor alpha (IL15:IL15Rα) complex. Most typically the immune effector cells are simultaneously exposed to the Ad5 vector and the IL-15:IL-15Rα complex. For example, contemplated IL-15:IL- 15Rα complexes comprises an IL-15N72D:IL-15RαSu/Fc complex (e.g., Nogapendekin alfa inbakicept (NAI), also known as N-803 or Alt-803) in which the Fc portion may be derived from any immunoglobulin, and especially from an IgG (e.g. IgG1, IgG4, etc). Alternatively, the IL-15:IL-15Rα complex may also be encoded in the Ad5 vector and then expressed and secreted from infected cells.

In further embodiments, the subject may or may not have been diagnosed with an infectious disease, a neoplastic disease, or cancer. Most preferably, the PBMC are derived by apheresis of the subject, and will comprise T cells, B cells, natural killer (NK) cells, natural killer T (NK-T) cells, dendritic cells, mast cells, myeloid derived phagocytes or combinations thereof.

Moreover, it is contemplated that the immunotherapeutic composition (after ex vivo infection) will be formulated for intravenous (IV) administration, which is typically used in the treatment of neoplastic disease, cancer, or infectious disease in a patient. For example, contemplated neoplastic diseases or cancers include bladder cancer, a glioblastoma, prostate cancer, hematological cancer, B-cell neoplasms, multiple myeloma, B-cell lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, colorectal cancer, ovarian cancer, non-small cell lung carcinoma, B cell non-Hodgkin lymphoma, squamous cell head or neck carcinoma, or urothelial/bladder carcinoma.

Additionally, it is contemplated that the treatment may further include radiation therapy, chemotherapy, surgery, and/or administration of a therapeutic antibody, an immunomodulatory agent, a proteasome inhibitor, a pan-DAC inhibitor, an H-DAC inhibitor, and/or a checkpoint inhibitor, and/or administration of an adoptive cell therapy comprising a CAR T and/or an NK cell therapy, and/or an immunotherapeutic agent.

Consequently, the inventors also contemplate a method of treatment of cancer or infectious disease that includes a step of performing therapeutic apheresis on a subject, a step of purifying the peripheral blood mononuclear cell (PBMC) fraction from the apheresis product, a step of exposing ex vivo the PBMC to at least one recombinant adenovirus subtype 5 (Ad5) vector comprising a deletion in an E1 gene region, a deletion in an E2b gene region, and a nucleic acid sequence encoding a peptide antigen, and a step of administering an effective amount of the Ad5 vector treated PBMC to a patient.

Such methods may also include a step of adding Interleukin 15 (IL15) or an IL15:IL15 receptor alpha (IL15:IL15Rα) complex to the ex vivo exposed PBMC. Additionally, or alternatively, the patient may also be pretreated with IL15 or an IL15:IL15Rα complex (e.g., N-803), and/or IL15 or an IL15:IL15Rα complex may be added to the Ad5 vector treated PBMC prior to administration. Similarly, IL15 or an IL15:IL15Rα complex may be administered to the patient subsequent to administration of the Ad5 vector treated PBMC. As will be readily appreciated, the administered cells may be obtained from the same individual or a different (e.g., at least haplocompatible) individual.

Various objects, features, aspects, and advantages of the inventive subject matter will become more apparent from the following detailed description of preferred embodiments, along with the accompanying drawing figures in which like numerals represent like components.

DETAILED DESCRIPTION

The inventors have now discovered various vaccine compositions and methods, and especially viral cancer vaccine compositions and methods that reduce or even entirely avoid adverse effects and/or drop in efficiency due to rapid attachment of therapeutic viruses to non-target tissue.

In especially preferred aspects, the recombinant therapeutic virus is administered ex vivo to cells of a subject diagnosed with cancer, wherein the cells are obtained from the subject by apheresis. In that context, it should be especially appreciated that apheresis can be used not only to isolate PBMCs but also to isolate erythrocytes and thrombocytes, which can also be used as therapeutic entities in a form as isolated, or after modification (e.g., transfection with recombinant nucleic acids, and especially mRNA). Additionally, natural killer (NK) cells can be isolated from the PBMC or via apheresis to yield yet another therapeutic modality in which the NK cells may further be genetically modified (e.g., to express a CAR) or stimulated to differentiate to cytokine-enhanced NK (CENK) or memory-type cytokine-enhanced (m-CENK) cells. As such, apheresis can be used to prepare various cell fractions other than PBMCs for treatment of the same patient in a concurrent or serial manner. Most typically, the treatments contemplated herein will at least comprise administration of ex vivo infected dendritic cells (that are most typically preferentially or selectively infected in the presence of other immune cells).

Figure 1:
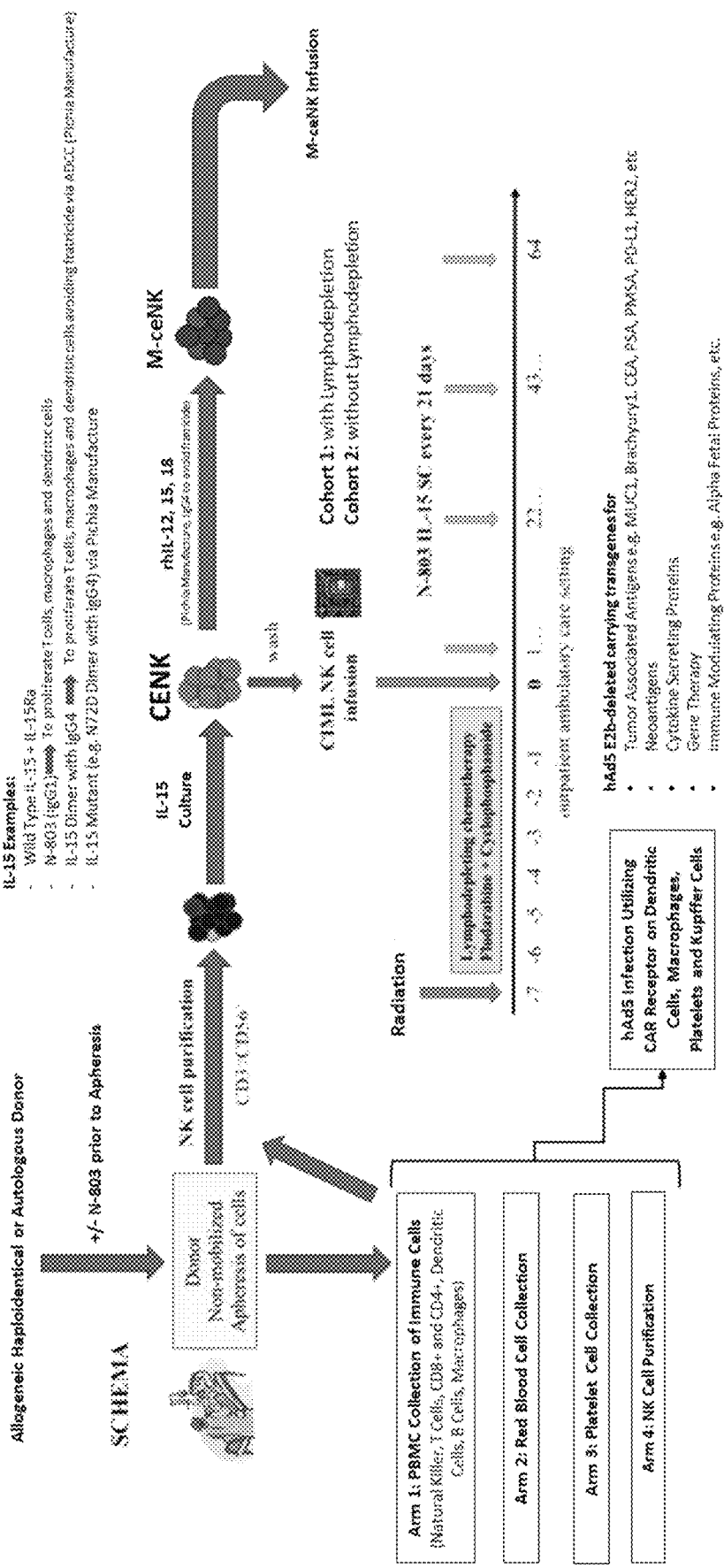
FIG. 1 is an exemplary schematic flow chart of a cancer treatment according to the inventive subject matter.

In one typical example, as schematically illustrated in FIG. 1, a subject diagnosed with cancer is optionally treated with N-803 to stimulate T-cell and NK-cell production prior to apheresis during which PBMCs are collected. During the same apheresis procedure, an erythrocyte-enriched cell fraction and a thrombocyte-enriched cell fraction can also be obtained from the same subject. Most typically, the PBMCs will include a variety of immune cells such as CD4$^+$ T cells, CD8$^+$ T cells, B cells, macrophages, dendritic cells, Kupffer cells, etc. As will be readily appreciated, the diverse mixture of cells can be immediately used for infection with a therapeutic virus (and especially a recombinant human adenovirus serotype 5 (hAd5)), leading to antigen presentation of the recombinant antigens encoded by the recombinant adenovirus on antigen presenting cells such as macrophages and dendritic cells. Consequently, the antigen presenting cells that present the recombinant neoantigens on the MHC class I and/or class II complexes will readily be in contact with unlicensed T cells, immature and mature unprimed T cells, (antigen-responsive) CD4$^+$ T cells and (antigen-responsive) CD8$^+$ T cells and as such will trigger development (activation and expansion) of antigen specific cytotoxic T cells. Alternatively, or additionally, the recombinant nucleic acid in the recombinant therapeutic virus need not be limited to a recombinant nucleic acid encoding one or more neoantigens or tumor associated antigens, but the recombinant nucleic acid may also encode a CAR that has specificity to a cancer-specific antigen of the cancer cell. Of course, it should be recognized that the infection of the lymphocytes with the recombinant therapeutic virus may be performed in the presence of immune stimulating cytokines (IL-2, IL-15, etc.), co-stimulatory molecules, and/or checkpoint inhibitors.

In especially contemplated compositions and methods, it is generally preferred that the PBMCs are exposed to the recombinant therapeutic virus for a time sufficient to induce measurable T cell expansion, and particularly clonal expansion of antigen-responsive T cells. As will be recognized, such expansion may be stimulated by addition of IL15, IL15:IL15Rα or an IL15Rβγ agonist derivative thereof, IL15:IL15RαIgG4Fc, or N-803 to the PBMC and therapeutic virus. In further preferred aspects, the PBMCs are exposed to the recombinant therapeutic virus for a time sufficient for the antigen presenting cells in the PBMC to take up substantially all of the recombinant therapeutic virus. Viewed form a different perspective, upon ex vivo infection, it is typically preferred that the viral titer in the PBMC supernatant is low to undetectable. Such time can be empirically ascertained by quantification of viral infectivity in the cell composition (e.g., using hexon assay where the virus is an adenovirus). Once T cell activation and/or expansion is observed and viral titer in the supernatant is low to undetectable, the so prepared cell suspension can then be used for infusion. Thus, by using contemplated methods and compositions, it should be appreciated that the infection of antigen presenting cells with the therapeutic virus is optimized while minimizing or entirely avoiding potential adverse effects due to off-target virus binding. The inventors also contemplate that the time of ex-vivo exposure be determined by MHC presentation of Ad-encoded peptides, wherein IV administration of Ad-treated apheresis product results in subsequent in vivo stimulation of antigen-responsive $CD4^+$ and $CD8^+$ T cells via MHC-presented antigen on the ex vivo infected cells.

In addition, it is contemplated that some of the apheresis product may also be subjected to isolation of NK cells, which may be expanded in vitro to provide additional cytotoxic effector cells. Moreover, and where desired, the isolated NK cells may be further stimulated to differentiate into cytokine enhanced NK cells (CENK) and/or memory-type cytokine enhanced NK cells (m-CENK). Alternatively, or additionally, at least some of the isolated NK cells may also be transfected with a recombinant nucleic acid to express on the cell surface a CAR with a target specificity of choice (e.g., neoantigen, or tumor associated antigen such as MUC1, Brachyury, CEA, PSA, PMSA, PD-L1, HER2, etc.). These modified NK cells can then be administered to the subject to thereby further augment the immunotherapeutic composition that includes the ex vivo infected apheresis product. Still further, it is contemplated that additional cell-based therapeutics may be administered such as haNK cells or t-haNK cells such as described, for example, in U.S. Pat. No. 11,643,452, and US 2021/0198342.

Moreover, it is contemplated that the apheresis may also yield erythrocytes and thrombocytes, which may be employed as additional therapeutic agents. For example, where a subject was previously subjected to chemotherapy or radiation, erythrocytes and thrombocytes may be preserved and administered, especially where chemotherapy or radiation was performed subsequent to apheresis. As should also be noted, the erythrocytes and/or thrombocytes may be genetically modified to express one or more proteins of interest (e.g., cytokine, checkpoint inhibitor, etc.).

With respect to the administration of the ex vivo infected apheresis composition, it is contemplated that the cells can be transfused to the subject as a stand-alone modality, or in combination with one or more immune stimulating cytokines. Most typically, where the administration also includes transfusion of NK cells (e.g., CENK, m-CENK, CAR-expressing NK cells, etc.), the NK cells will preferably be administered after the ex vivo infected apheresis composition, for example, at least 1 day, or at least three days, or at least seven days, or at least 14 days after transfusion of the ex vivo infected apheresis composition.

Figure 2:
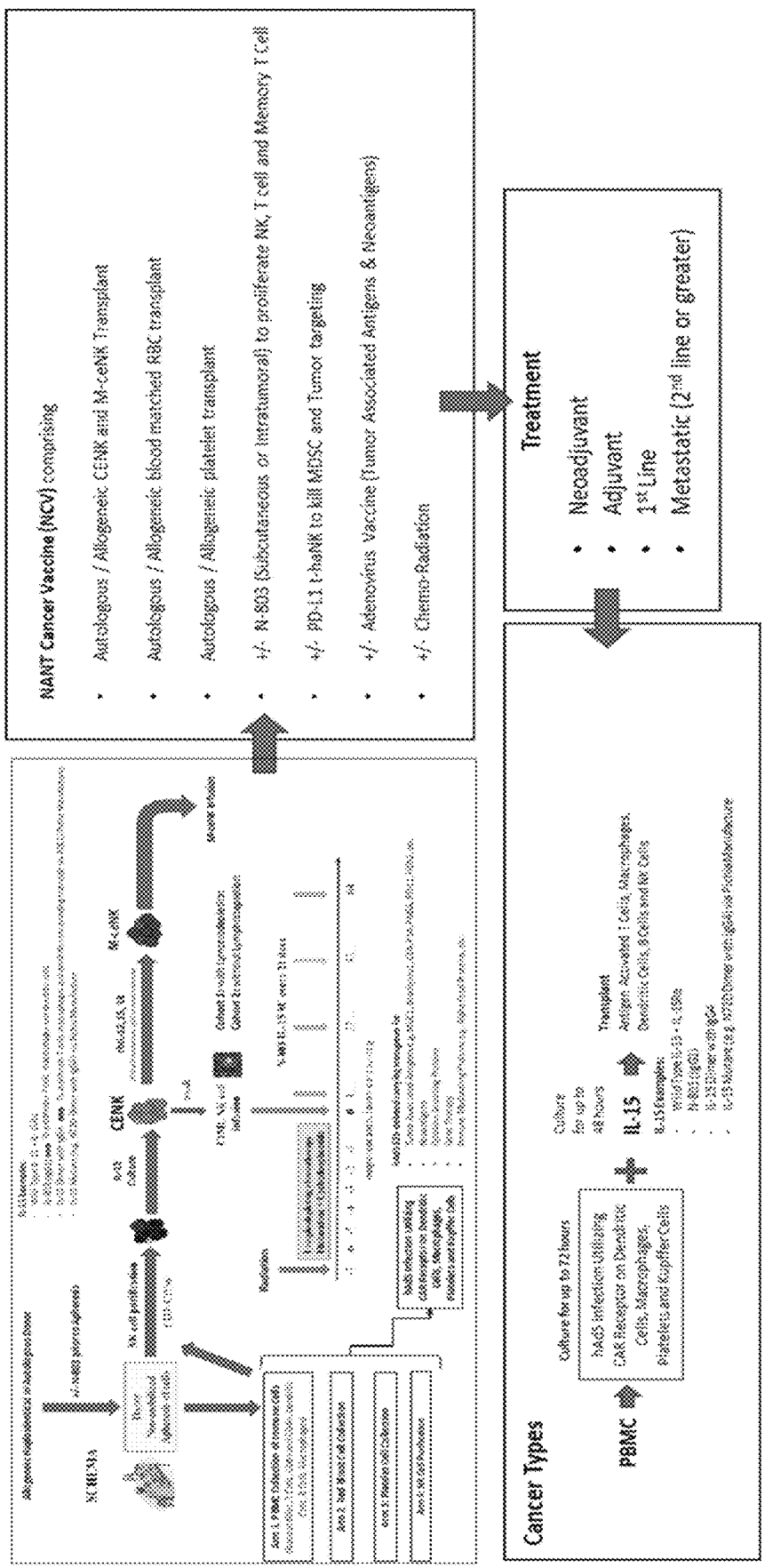
FIG. 2 is an exemplary schematic flow chart of another cancer treatment according to the inventive subject matter.

FIG. 2 exemplarily and schematically illustrates treatment options and components using the ex vivo infected apheresis composition. As can be readily taken from FIG. 2, treatment protocols in addition to the ex vivo infected apheresis composition will include autologous or allogeneic CENK and/or m-CENK transplants, autologous or allogeneic blood matched red blood cell transplants, autologous or allogeneic platelet transplants. Moreover, treatment schemes contemplated herein will also include supportive administration of IL-15, IL15:IL15Rα constructs, or N-803 (subcutaneous or intratumoral) or other cytokines (e.g., NHS-IL-12, see *Immunotargets Ther.* 2021; 10: 155-169), for example, to help proliferate NK cells, T cells, and memory T Cells. Moreover, PD-L1 t-haNK cells may be administered to the patient to kill myeloid derived suppressor cells (MDSC) and to target tumor cells that express PD-L1. Furthermore, contemplated treatments may also include chemotherapy and/or radiation, and in some instances treatment with a recombinant therapeutic virus (e.g., administered intratumorally). As such, contemplated treatment regimens may be used as neoadjuvant treatment or as adjuvant treatment for first line treatment of for treatment of metastatic or recurrent disease.

Figure 3:
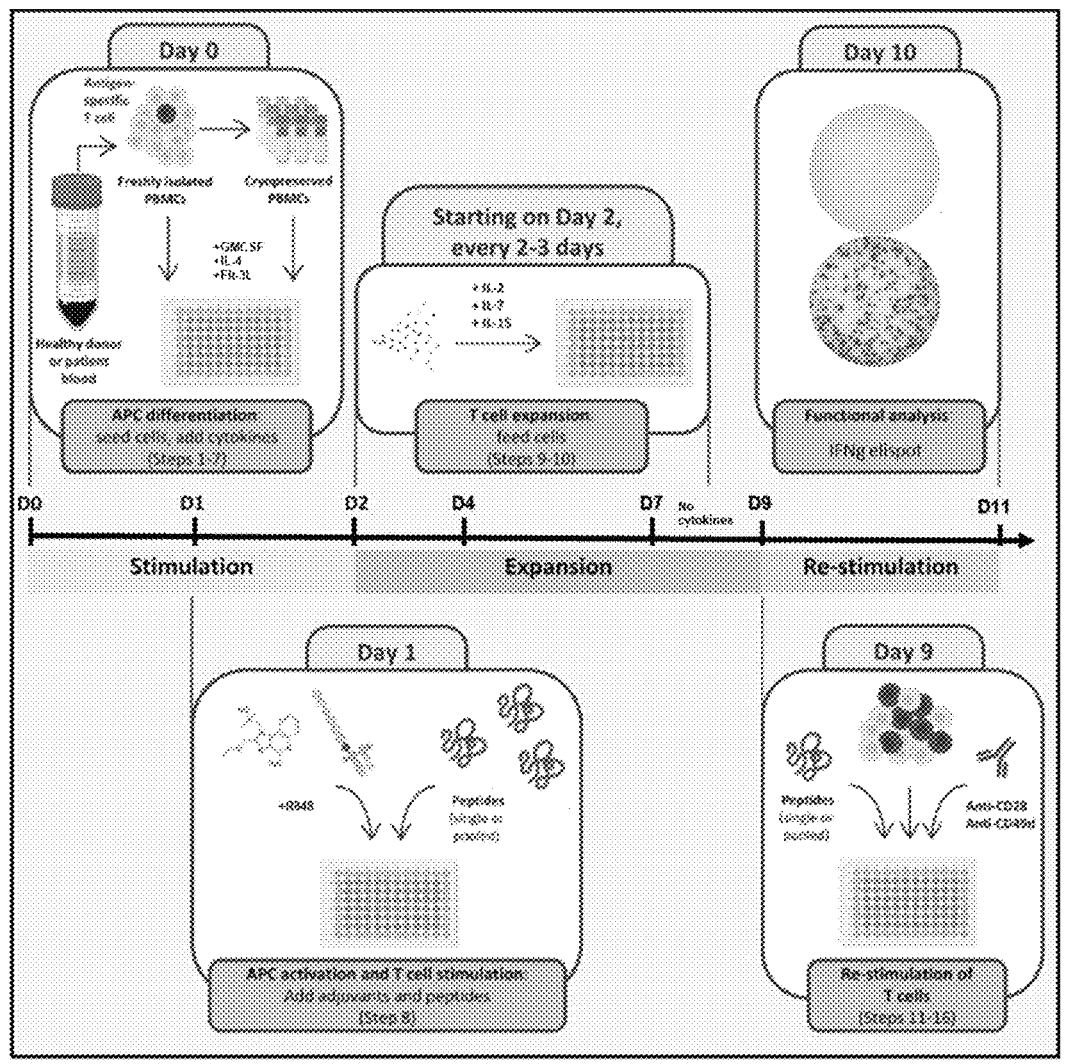
FIG. 3 is an exemplary schematic flow chart for selective ex vivo PBMC Ad5 infection.
Figure 4:
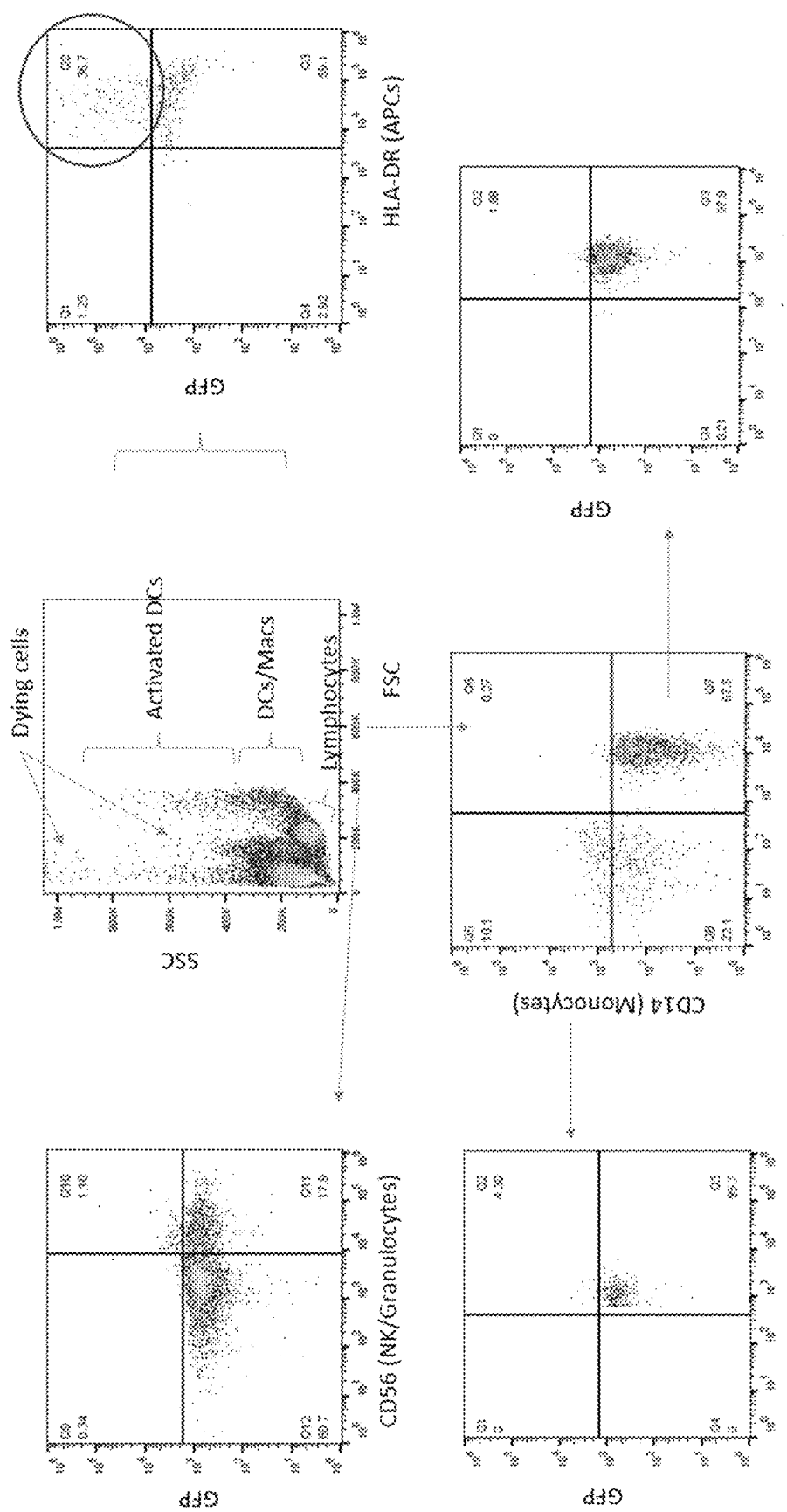
FIG. 4 depicts exemplary results for Ad5 infection of PBMCs using an MOI of 1000 according to the inventive subject matter.

With regard to ex vivo infection of PBMCs, FIG. 3 shows an exemplary workflow using previously frozen PMBC from a leukopak (LP186). More specifically, human peripheral blood mononuclear cells (PBMCs) were isolated from a leukopak using Ficoll Paque gradient, and then frozen in liquid nitrogen. To test the ability of AdV to transduce dendritic cells in a mixed cell population, PBMCs were thawed and cultured in XVIVO15 media with GM-CSF and FLT3L for 24 hours at 37° C. Next, the cells were transduced with AdV-GFP (recombinant adenovirus encoding green fluorescent protein as marker) at the below indicated multiplicity of infection (MOI) for 24 hours, and then analyzed by flow cytometry. While FIG. 3 shows peptide antigen stimulation, the inventors also performed stimulation with AdV-GFP as shown in the data below. Antibodies for cell-type specific surface markers were used to identify granulocytes (CD56), antigen presenting cells (HLA-DR), monocytes (CD14), and T-cells (CD3). Individual cell types were gated and examined for GFP expression using Flowjo software. Notably, the results in FIG. 4 show that only HLA-DR positive antigen presenting cells exhibited GFP expression.

Figure 5:
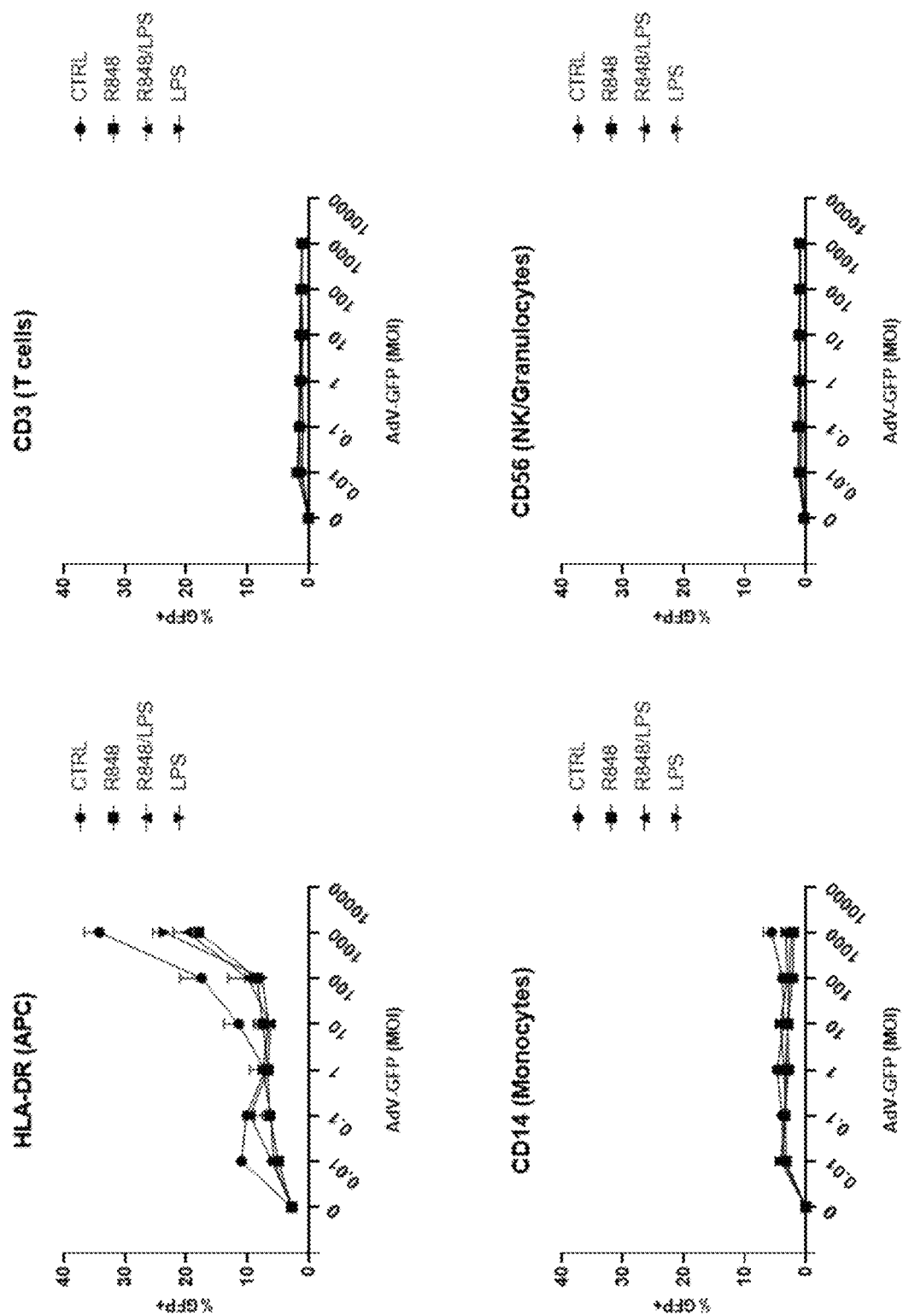
FIG. 5 depicts exemplary results for Ad5 infection at varying MOIs according to the inventive subject matter.

To test the effects of adjuvant on APC transduction by AdV-GFP, PBMCs were transduced and analyzed as described above with the concurrent addition of a TLR7/8 ligand reziquimod (R848), a TLR4 ligand lipopolysaccharide (LPS), or both. Unexpectedly, the results in FIG. 5 show that concurrent addition of the TLR ligands (TLR7/8 ligand and TLR4 ligand) with AdV-GFP transduction resulted in a decrease of transduction efficiency across almost the entire range of tested MOIs.

Based on the results obtained in the above experiments, the inventors then contemplated that fresh or frozen PBMCs obtained from a subject can be treated with GM-CSF and FLT3L for a time sufficient to allow for antigen presenting cells to differentiate (e.g., 8-16 hours, or 12-24 hours, or 18-36 hours, or 24-48 hours), typically also in the presence of Interleukin 4 (IL-4). Subsequently, the so treated cells are then stimulated, optionally in the presence of one or more TLR ligands, such as with a peptide antigen(s), an inactivated virus, a recombinant virus (e.g., Ad5 virus with recombinant nucleic acid encoding one or more cancer antigens, cancer associated antigens, and/or patient and tumor specific neoantigens) or other pathogen to so activate the antigen presenting cells. The so differentiated and stimulated cells are then fed, and the T cell sub-population is expanded in the presence of the activated antigen presenting cells using fresh medium containing suitable cytokines (e.g., IL-2, IL-7, IL-15). Most preferably, the so obtained cell population is then once more stimulated (preferably in the presence of anti-CD28 and/or anti-CD49d antibodies) with the peptide antigen(s), the inactivated virus, the recombinant virus or other pathogen for at least 6-8 hours. Where desired, the T cells can then be tested for function (e.g., IFN-gamma secretion in a conventional ELISpot assay) prior to transfusion to the subject.

As should be readily appreciated, the initial stimulation with the peptide antigen(s), the inactivated virus, the recombinant virus or other pathogen can be performed at dosages, or relative concentrations of viral particles to antigen presenting cells, that are substantially higher than would otherwise be achieved in an in vivo stimulation. Moreover, the re-stimulation can equally use significantly higher quantities than would be administered in vivo. Indeed, the peptide antigen(s), the inactivated virus, the recombinant virus or other pathogen can readily be removed after (re-) stimulation by simply exchanging the medium prior to administration to the subject. As such, it should be recognized that high transfection efficiencies can be achieved with the subject's antigen presenting cells in the ex vivo protocol while entirely avoiding systemic side effects or loss of recombinant virus to non-specific infection or adhesion of the viral particles to non-target tissue. Advantageously, and particularly where a recombinant Ad5 virus is employed, transfection is selective to antigen presenting cells (and especially dendritic cells) and does not adversely affect other cell types in the PBMC preparation (and especially T cells) that will be reactive to the antigens presented by the transfected antigen presenting cells.

For example, in some embodiments, the PBMCs are exposed to the recombinant therapeutic virus for a time sufficient for the antigen presenting cells in the PBMC to take up substantially all of the recombinant therapeutic virus (during stimulation and/or re-stimulation). Among other options, suitable times will be between 60 and 180 minutes, or between 180 and 600 minutes, or between 8 and 12 hours, or between 12-24 hours, and even longer, typically at a MOI of between 1:1 and 100,000 (and even more typically between a MOI of 100 and 50,000. Alternatively, and as already mentioned above, residual viruses can be removed and reduced in number by replacement of the medium in which the cells are maintained or grown. Thus, it should be appreciated that, upon ex vivo infection, the viral titer in the PBMC supernatant is low to undetectable (e.g., equal or less than $10^4$ viral particles per mL, equal or less than $10^3$ viral particles per mL, equal or less than $10^2$ viral particles per mL, or even less).

Where recombinant viruses are used for ex vivo transfection, it is generally preferred that the ex vivo infection of the PBMC is preferential or even selective with regard to antigen presenting/dendritic cells in the PBMC preparation as compared to non-dendritic cells (e.g., antigen presenting/dendritic cells have the highest rate of transfection, or antigen presenting/dendritic cells have a rate of transfection that is at least 5 or at least 10, or at least 50, or at least 100 fold of the rate of transfection of a non-dendritic cell sub-population (e.g., T cell, NK cell, monocytes, etc.). Therefore, recombinant adenoviruses are particularly preferred.

It is still further preferred that the ex vivo transfection of the antigen presenting/dendritic cells is performed in the presence of other immune cells such as macrophages, monocytes, T cells, B cells, etc. As will be readily appreciated, such mixed cell population will be suitable to direct exposure of the processed and presented antigens to T cells (and especially CD4+ and CD8+ T cells), resulting in a cell population that can be transfused to a subject to elicit an effective immune response against the antigen that is encoded in the recombinant virus and expressed in the transfected cells.

Therefore, in an embodiment, the inventors contemplate an immunotherapeutic composition comprising a patient-derived apheresis product comprising peripheral blood mononuclear cells (PBMC), and a human adenovirus serotype 5 (hAd5) vector comprising a deletion of the early 1 [E1] and early 2b [E2b] genes, and a nucleic acid encoding at least one immunogenic peptide sequence. In this context, it is noted that the term "human adenovirus serotype 5 (hAd5) vector" encompasses a recombinant hAd5 nucleic acid as well as a recombinant hAd5 viral particle containing a recombinant hAd5 nucleic acid. The composition is for use in generating 1) a cellular vehicle for administration of the Ad5 vector to a patient in need thereof; 2) an ex vivo composition comprising antigen presenting cells (APC) expressing MHC presented immunogenic peptides encoded by the Ad5 nucleic acid; and/or 3) activated T cells, wherein the T cells have been stimulated to proliferate by T cell receptor (TCR) mediated contact with the APC cells.

In an embodiment, the immunotherapeutic composition is determined by exposure time, wherein the composition comprises PBMC and Ad5 vector, wherein the duration of ex vivo exposure of PBMC to Ad5 is determined by the desired composition outcome (1-3 above).

In an embodiment, the composition comprises Ad5 vector encoding at least one antigenic peptide, PBMC-derived activated T cells and IL-15 or an IL15Rβγ agonist derivative thereof. In an embodiment, the composition comprises activated T cells and N-803. IL-15 may act to facilitate binding between APC-expressed IL15Rα and T cell-expressed IL15Rβγ. N-803 will stimulate expansion of activated T cells. In an embodiment, the composition further comprises 3M-052 (Toll-Like Receptor (TLR) 7/8 stimulant).

In an embodiment, the composition is for use in the treatment of cancer or infectious disease. The Ad5 encoded immunogenic peptide may encode a tumor associated antigen, a tumor specific antigen, or a neoantigen. The Ad5 encoded immunogenic peptide may encode a viral, yeast, or bacterial antigen. Identification of an antigenic sequence may derive from tumor normal sequencing, mRNA expression, and peptide expression analysis of normal and diseased tissue. For example, tumor versus normal sequencing can be performed using algorithms as described in U.S. Ser. No. 10/971,248, U.S. Ser. No. 10/991,451, and U.S. Ser. No. 11/133,085.

In an embodiment, the composition comprises an Ad5 vector, wherein the nucleic acid encodes alpha fetoprotein. In an embodiment, the composition comprises 1) an Ad5 vector, wherein the nucleic acid encodes alpha fetoprotein, 2) Granulocyte Macrophage Colony Stimulating Factor (GMCSF), and 3) interleukin 4 (IL-4). In this embodiment, the composition is for use in the treatment of ulcerative colitis.

In an embodiment, the inventors conceive of a method of treatment, wherein the composition is administered to a patient in need thereof. The method comprises intravenous (IV) administration of the composition to the patient. The method further comprises subcutaneous administration of IL-15, IL15:IL15Rα or a derivative thereof, or N-803 (IL-15 superagonist) to the patient. The method further comprises administration of one or more agents comprising the Nant Cancer Vaccine as described, for example, in US 2023/0034802; U.S. Pat. Nos. 11,207,392; 11,071,774; and 11,439,697). The method may further comprise surgery and/or radiation.

In an embodiment, the composition comprises NK cells, wherein the NK cells are purified from the apheresis product. NK cells are screened out by flow sorting or other method. NK cells are identified as CD56+/CD3−. The NK cells are combined ex vivo with an Ad5 vector comprising a nucleic acid encoding at least one Chimeric Antigen Receptor. Optionally, the composition further comprises IL-15, IL15:IL15Rα or a derivative thereof, or N-803. The NK cells may be activated and expanded from PBMC as previously described in U.S. Pat. No. 11,453,862; US 2021/0009954; and/or activated and expanded to produce CIML-NK cells as described in US 20210008107; US 2021/0008112; US 20210361711; Alternatively, or additionally, NK cells may be differentiated to mCENK cells as described in WO/2022/187207. Where the NK cells are transfected with a recombinant nucleic acid to express a CAR, especially contemplated compositions and methods are described in US 2022/0282216. Contemplated compositions are for use in the treatment of cancer or infectious disease. Also contemplated is a method of treatment wherein contemplated compositions are administered IV to a patient in need thereof. The method further comprises subcutaneous administration of IL-15, IL15:IL15Rα or a derivative thereof, or N-803 (IL-15 superagonist) to the patient. The method further comprises administration of one or more agents comprising the Nant Cancer Vaccine as is known from US 2023/0034802; U.S. Pat. Nos. 11,207,392; 11,071,774; and 11,439,697.

In an embodiment, the sorted NK cells are cultured in IL15 and optionally glucocorticoid, followed by an expansion phase wherein the NK cells are cultured in IL15/IL18/IL12 whereby memory cytokine-enriched natural killer (m-CENK) cells are induced. See e.g., WO/2022/187207 The m-ceNK cells can be further genetically engineered to express a CAR with specificity for a cancer or infectious disease antigen. The m-ceNK cells can be for autologous administration in combination with the stimulated T cells of the present invention. The m-CENK cells can be for autologous or allogeneic haploidentical administration, in conjunction with IV administration of the Ad5 treated apheresis product of the present invention. The m-CENK cells can be administered in conjunction with a tumor specific antibody or a checkpoint inhibitor antibody. Alternatively, the IL15-expanded NK cells can be administered as an adjunct to lymphodepleting chemotherapeutics administered in conjunction with IV administration of the Ad5 treated apheresis product of the present invention.

In an embodiment, the inventors conceive of a method of induction of differential ex vivo expansion of antigen-specific T cells, the method comprising exposing patient-derived apheresis product comprising peripheral blood mononuclear cells (PBMC), to a human adenovirus serotype 5 (hAd5) vector comprising a deletion of the early 1 [E1] and early 2b [E2b] genes and a nucleic acid encoding at least one immunogenic peptide sequence, for a time sufficient to induce measurable T cell expansion. The method may further comprise addition of IL15, IL15:IL15Rα or an IL15Rβγ agonist derivative thereof, IL15:IL15RαIgG4Fc, or N-803 to the PBMC and Ad5 vector, whereby T cell stimulation is enhanced. In an embodiment, the differentially stimulated T cells are specific for a tumor antigen or neoantigen. In an embodiment, the differentially stimulated T cells are specific for an infectious disease antigen.

In an embodiment, the inventors conceive of a method of IV administration of hAd5 vectors comprising a deletion of the early 1 [E1] and early 2b [E2b] genes and a nucleic acid encoding at least one immunogenic peptide sequence, wherein the toxicity of IV or subcutaneous administration of said Ad5 vector is mitigated by cellular uptake and therefore cell-mediated delivery of the Ad5 vectors via IV administration to a patient, the method comprising exposing patient-derived apheresis product comprising peripheral blood mononuclear cells (PBMC) to a human adenovirus serotype 5 (hAd5) vector comprising a deletion of the early 1 [E1] and early 2b [E2b] genes and a nucleic acid encoding at least one immunogenic peptide sequence, for a time sufficient for the APC of the apheresis product PBMC to take up the Ad5 vectors, wherein the viral titer of the PBMC supernatant is effectively nil.

In an embodiment, the inventors conceive of a method of inducing antigen expression in apheresis product (PBMC-derived) antigen presenting cells, the method comprising exposing patient-derived apheresis product comprising peripheral blood mononuclear cells (PBMC), to a human adenovirus serotype 5 (hAd5) vector comprising a deletion of the early 1 [E1] and early 2b [E2b] genes and a nucleic acid encoding at least one immunogenic peptide sequence, for a time sufficient to induce immunogenic peptide expression on the surface of the PBMC-derived APC.

In an embodiment, the inventors conceive of the addition of IL15:IL15RαIgG4Fc to the ex vivo composition comprising PBMC and Ad5 vector. The IgG4 moiety provides stability to the IL15:IL15Rα construct but abrogates the ability to draw endogenous NK cells to the T cells which are bound and stimulated by IL15:IL15RαIgG4Fc, as the IgG4Fc does not bind to the Fc receptor (CD16) on the NK cell. The antibody dependent cell cytotoxicity of the NK cell interacting with the IgG1 of the N-803 is therefore blocked.

In an embodiment, the patient is administered (subcutaneously) IL15, IL15:IL15Rα or an IL15Rβγ agonist derivative thereof, IL15:IL15RαIgG4Fc, or N-803 prior to apheresis.

In an embodiment, red blood cells are purified from the apheresis product. The RBC can be engineered to express one or more therapeutic proteins. The RBC can be expanded and differentiated into enucleated mature RBC and formulated for IV administration along with Ad5 treated apheresis product.

In an embodiment, platelets are purified from the apheresis product. The platelets can be engineered to express one or more therapeutic proteins (typically from RNA). The platelets can be formulated for IV administration along with Ad5 treated apheresis product.

In embodiments, the hAd5 E2b-deleted vector comprises transgenes for tumor associated antigens (e.g., MUC1, Brachyuryl, CEA, PSA, PMSA, PD-L1, HER2 . . . ), and/or neoantigens. In embodiments, the hAd5 E2b-deleted vector further comprises transgenes encoding cytokines, gene therapy, immune modulating proteins, alpha fetoprotein, checkpoint inhibitors, and co-stimulatory proteins.

In embodiments, the apheresis product derived PBMC are exposed to hAd5 vectors comprising a deletion of the early 1 [E1] and early 2b [E2b] genes and a nucleic acid encoding at least one immunogenic or therapeutic peptide sequence. The exposure time may be at least one hour, at least 2 hours, at least 4 hours, at least 8 hours, at least 16 hours, at least 24 hours, at least 48 hours, at least 72 hours, at least 4 days, at least 6 days, or at least 8 days.

The inventors also conceive of a method of optimizing hAd5 uptake in an ex vivo composition comprising patient-derived apheresis product comprising peripheral blood mononuclear cells (PBMC), and a human adenovirus serotype 5 (hAd5) vector comprising a deletion of the early 1 [E1] and early 2b [E2b] genes and a nucleic acid encoding at least one immunogenic peptide sequence, wherein the optimal exposure time is empirically determined by loss of Ad5 infectivity in the apheresis product supernatant. Infectivity may be indirectly determined, for example, by hexon assay of the supernatant.

In still further contemplated aspects, various exemplary methods are contemplated. For example:

Experiment 1: Test of N-803 vs. IL15:IL15RαSuIgG$_4$ to determine the effect of the IgG$_4$ Fc portion on T cell activation and/or fratricide via antibody dependent cell cytotoxicity. Here, it is contemplated that the various test agents with IL-15 activity such as IL-15, N-803, IL15: IL15RαSuIgG$_4$, etc. are added to the apheresis derived PBMC fraction in the presence of Ad5/tumor antigen. Alternatively, CEFT can be used to pulse the PBMCs, and subsequent T cell activation/proliferation evaluated in the presence of IL15, IL15:IL15RαSu, IL15:IL15RαSuIgG$_4$, or N803.

Experiment 2: optimization of ex vivo uptake, antigen presentation, and/or T cell stimulation. Here, viral uptake can be measured using a recombinant Ad5 virus that encodes GFP or other reporter gene, which can then be used to identify optimized multiplicity of infection (MOI). The same test system can also be used to monitor Ad5 uptake (and conversely virus clearance from the supernatant) either using the recombinant Ad5 virus or an Ad5 null virus. In such systems, the hexon assay may be employed to quantify residual virus in the cell supernatant. In addition, the in vitro system may also be used to quantify MHC expression and MHC-mediated antigen presentation of the antigen presenting cells (e.g., via flow cytometry or ELISPOT assay). As will be readily appreciated, antigen presentation may be further stimulated by coincubation with various ligands such as GMCSF, IL4, and/or Flt3 ligand. Still further, it should be noted that T cell stimulation and proliferation can be determined in such in vitro systems using ELISPOT or other assays. Where desired, effects of adjuvants, costimulatory molecules (e.g., (CD40 ligand, GITR ligand, Ox40 ligand, etc., which may be encoded in the recombinant Ad5) or checkpoint inhibitors can be assessed in vitro.

Experiment 3: Stimulation of memory vs. de novo immunity. Here, contemplated systems for memory immunity may employ a test with a universal antigenic sequence (e.g., wt Ad5 peptides absent from E1-, E2B-vectors, SARS-COV-2 Spike or nucleocapsid proteins) or an antigenic sequence for which the individual from which PMBC were obtained is immune (e.g., from known prior exposure or vaccination). Alternatively, de novo immunity can be elicited using standard vaccines (e.g., adenoviral vaccine formulations encoding or expressing Brachyury, CEA, MUC1, PSA, etc.).

Experiment 4: Optimization of MHC antigen peptide presentation: Various vaccine formulations can be tested in vitro to ascertain effect of intracellular trafficking, inclusion of recombinant co-stimulatory molecules and/or cytokines, etc. on the antigen presentation. Such test systems will preferably include quantification of MHC-presented antigens and/or cell proliferation of antigen-responsive T cells. Antigen presentation can be optimized using subcellular localization tags genetically engineered onto the N or C terminus of the antigenic peptide.

Experiment 5: Comparison of SubQ versus Ex Vivo Administration. Here, an animal system may be used to determine the quantitative differences in immune response between SubQ administered formulations and treated apheresis product administered by transfusion in a medium suitable for cell transfusion (e.g., 5% human serum albumin in 0.9% sodium chloride). The efficacy can be measured by antigen-specific T cells in vitro (e.g., using ELISPOT assay). For example a C57BL16 inbred mouse model can be used for both 1) SubQ administered Ad5 vaccine and 2) IV administered ex vivo apheresis product exposed to Ad5 vaccine.

In some embodiments, the numbers expressing quantities of ingredients, properties such as concentration, reaction conditions, and so forth, used to describe and claim certain embodiments of the invention are to be understood as being modified in some instances by the term "about." As used herein, the terms "about" and "approximately", when referring to a specified, measurable value (such as a parameter, an amount, a temporal duration, and the like), is meant to encompass the specified value and variations of and from the specified value, such as variations of +/−10% or less, alternatively +/−5% or less, alternatively +/−1% or less, alternatively +/−0.1% or less of and from the specified value, insofar as such variations are appropriate to perform in the disclosed embodiments. Thus, the value to which the modifier "about" or "approximately" refers is itself also specifically disclosed. The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. An immunotherapeutic composition, comprising:
   1) Subject-derived peripheral blood mononuclear cells (PBMC), granulocyte macrophage colony stimulating factor (GM-CSF), and FMS-like tyrosine kinase 3 (Flt-3) ligand,
   2) at least one recombinant adenovirus subtype 5 (Ad5) vector comprising a deletion in an E1 gene region, a deletion in an E2b gene region, and a nucleic acid sequence encoding a peptide antigen, and
   2) Immune-stimulating cytokines comprising a) Interleukin-15 (IL-15) or an IL-15: IL-15 receptor alpha (IL15: IL15Rα) complex, b) IL-2, and c) IL-7,
   wherein the PBMC are simultaneously exposed to the Ad5 vector and the immune stimulating cytokines.

2. The immunotherapeutic composition of claim 1, wherein the IL15: IL15Rα complex comprises an IL-15N72D: IL15RαSu/Fc complex (N-803).

3. The immunotherapeutic composition of claim 1, wherein the subject has been diagnosed with an infectious disease, a neoplastic disease, or cancer.

4. The immunotherapeutic composition of claim 3, wherein the neoplastic disease or cancer comprises bladder cancer, a glioblastoma, prostate cancer, hematological cancer, B-cell neoplasms, multiple myeloma, B-cell lymphoma, Hodgkin's lymphoma, chronic lymphocytic leukemia, acute myeloid leukemia, cutaneous T-cell lymphoma, T-cell lymphoma, a solid tumor, urothelial/bladder carcinoma, melanoma, lung cancer, renal cell carcinoma, breast cancer, gastric and esophageal cancer, head and neck cancer, colorectal cancer, ovarian cancer, non-small cell lung carcinoma, B cell non-Hodgkin lymphoma, squamous cell head or neck carcinoma, or urothelial/bladder carcinoma.

5. The immunotherapeutic composition of claim 1, wherein the PBMC comprise T cells, natural killer (NK) cells, natural killer T (NK-T) cells, dendritic cells, mast cells, myeloid derived phagocytes or combinations thereof.

6. The immunotherapeutic composition of claim 1, wherein the immunotherapeutic composition is formulated for intravenous (IV) administration.

* * * * *